United States Patent [19]

Kurihara et al.

[11] Patent Number: 5,051,402
[45] Date of Patent: Sep. 24, 1991

[54] PHARMACEUTICAL COMPOSITION CONTAINING CYCLOSPORIN IN ADMIXTURE WITH α-CYCLODEXTRIN

[75] Inventors: Kozo Kurihara; Masaru Murano, both of Tokyo, Japan

[73] Assignee: Sankyo Company, Limited, Tokyo, Japan

[21] Appl. No.: 587,580

[22] Filed: Sep. 21, 1990

Related U.S. Application Data

[63] Continuation of Ser. No. 201,579, Jun. 1, 1988, abandoned.

[30] Foreign Application Priority Data

Jun. 4, 1987 [JP] Japan ............................ 62-140703

[51] Int. Cl.$^5$ .............................................. A61K 37/02
[52] U.S. Cl. .......................................... 514/11; 514/9; 514/885
[58] Field of Search ................ 514/11, 9, 58, 885, 514/970; 530/321, 317; 536/103

[56] References Cited

U.S. PATENT DOCUMENTS 4,117,118  9/1978  Härri et al. ........................ 530/321

4,388,307  6/1983  Cavanak ............................ 424/177

FOREIGN PATENT DOCUMENTS 895724   7/1983  Belgium .
94157   11/1983  European Pat. Off. .
0170623  2/1986  European Pat. Off. .
2015339  9/1979  United Kingdom .

OTHER PUBLICATIONS

Stadler–Szöke et al., Proceedings of the First Int. Symp. on Cyclodextrins, Szejtli (ed.), D. Reidel Publishing Co., Boston, U.S.A., pp. 377–388 (1981).
Merck Index, 10th Edition, 1983, p. 396, No. 2748.

*Primary Examiner*—John Doll
*Assistant Examiner*—Christina Chan
*Attorney, Agent, or Firm*—Frishauf, Holtz, Goodman & Woodward

[57] ABSTRACT

Cyclosporins are useful immunosuppressive, anti-fungal and antiphlogistic agents which are relatively insoluble in water and aqueous fluids (including body fluids). They may be rendered more soluble by the concomitant administration of α-cyclodextrin, either separately, but essentially simultaneously or, preferably, in admixture.

33 Claims, No Drawings

PHARMACEUTICAL COMPOSITION CONTAINING CYCLOSPORIN IN ADMIXTURE WITH α-CYCLODEXTRIN

This application is a continuation of application Ser. No. 07/201,579, filed June 1, 1988, now abandoned.

BACKGROUND OF THE INVENTION

The present invention relates to a novel pharmaceutical composition wherein at least one cyclosporin is the active ingredient and is accompanied by a solubilising agent which is α-cyclodextrin and/or a derivative thereof.

The cyclosporins are a homologous group of biologically active oligopeptides, which are metabolites produced by certain fungi imperfecti. Cyclosporin A is the best known member of this group, but cyclosporins B to I have also so far been identified, and the commercially available product may contain a mixture of several separate individual cyclosporins. They all share a cyclic peptide structure consisting of 11 amino acid residues with a total molecular weight of about 1,200, but with different substituents or configuration of some of the amino acids.

For convenience, the term "cyclosporin" (in the singular and without further qualification) will be used hereinafter to designate the cyclosporin component in the composition of the present invention. However, it should be understood that, as used with reference to the invention, this term is intended to include any individual member of the cyclosporin group, as well as mixtures of two or more such individual cyclosporins whether in the form of commercially available mixtures or otherwise.

Cyclosporin has immunosuppressive, antifungal and antiphlogistic activities, but has so far been primarily used therapeutically for its immunosuppressive activity. In its therapeutic use as an immunosuppressive, it is currently used either orally or by injection. However, since the solubility of cyclosporin in water is extremely low (e.g. 20 µg/ml to 30 µg/ml for cyclosporin A), both types of formulation are prepared as an oily solution containing ethanol. Even so, the bioavailability of its oral preparations is extremely low, generally below 30% [K. Takada et al, Drug Delivery System 1, No. 1, 1-7 (1986)]. This is believed to be due to the separation of cyclosporin as a solid immediately after it comes into contact with water, e.g. in the mouth or in the gut. Injectable preparations of cyclosporin formed as an oily solution containing ethanol have first to be diluted with physiological saline before intravenous administration. In the case of intravenous administration, however, it is clearly not merely undesirable, but highly dangerous for cyclosporin to separate out on contact with water. Accordingly, a surface active agent, such as a polyoxyethylated castor oil, is added as a solubilizer to injectable preparations in order to prevent the cyclosporin from separating out. However, the addition of surface active agents, such as polyoxyethylated castor oil, to injectable preparations can give rise to safety problems.

Cyclosporin is effective in the treatment of the ocular symptoms of Behcet's Syndrome. If it is administered orally for the treatment of these symptoms and relies upon systemic circulation to reach the eyes, the side effects of the drug may cause various adverse reactions, such as hypertrichosis or renal dysfunction. However, if oily preparations containing cyclosporin are applied directly to the eyes, irritation or a clouded visual field may result. Hence, cyclosporin is, in practice, of little practical use in the treatment of the ocular symptoms of Behcet's Syndrome, for which it would otherwise be well suited. Moreover, if it were possible to prepare a formulation suitable for topical application to the eyes, it would be expected to have various other uses in addition to the treatment of the ocular symptoms of Behcet's Syndrome. For example, from its pharmacological mode of action, it is though that it could be useful during keratoplasty, as well as in the treatment of herpetic keratitis and spring catarrh.

One way of overcoming this problem would be to dissolve sufficient cyclosporin in an aqueous solvent system so as to reach an effective concentration for treatment. Such a solvent system should not contain any additive, such as a surface active agent, which could give rise to safety problems. If this could be achieved, the cyclosporin would already be in an aqueous solution and its contact with bodily fluids would merely constitute dilution, so that it would not immediately separate out when contacted with the water of such fluids. However, so far it has been very difficult to make any such preparation because cyclosporin has an extremely low solubility in water and has a cyclic structure with a molecular weight significantly greater than 1,000, with the result that a sufficient amount cannot be dissolved to be effective for the desired treatment. For instance, Table 1 shows the solubility of cyclosporin A in various kinds of solvents, from which it can be seen that the solubility pattern seems quite unique.

TABLE 1

| Solvent | Solubility parameters | | | Solubility of cyclosporin A [mg/ml] |
|---|---|---|---|---|
| | δd | δp | δh | |
| Methanol | 7.4 | 6.0 | 10.9 | >1000 |
| Ethanol | 7.7 | 4.3 | 9.5 | >1000 |
| Acetonitrile | 7.5 | 8.8 | 3.0 | >1000 |
| Ethyl acetate | 7.4 | 2.6 | 4.5 | >1000 |
| Benzene | 8.9 | 0.5 | 1.0 | 400 |
| Tetrahydrofuran | 8.2 | 2.8 | 3.9 | 400 |
| Acetone | 7.6 | 5.1 | 3.4 | 100 |
| Propylene glycol | 8.2 | 4.6 | 11.4 | 100 |
| Isopropanol | 7.7 | 3.0 | 8.0 | 50 |
| Cyclohexane | 8.2 | 0.0 | 0.0 | 20 |
| Hexane | 7.2 | 0.0 | 0.0 | <10 |
| Water | 6.0 | 15.3 | 16.7 | <1 |

In the above Table, $\delta d$, $\delta p$ and $\delta h$ are measures of dispersion force, polarity and hydrogen bonding, respectively.

In view of these solubility properties, it has, in the past, been considered not merely difficult, but practically impossible to prepare a pharmaceutical composition containing cyclosporin dissolved in an aqueous medium.

We have now surprisingly found that this long-felt want can be met by incorporating α-cyclodextrin into a pharmaceutical preparation.

BRIEF SUMMARY OF INVENTION

Thus, in accordance with the present invention, there is provided, as a new composition of matter, a pharmaceutical composition comprising at least one cyclosporin in admixture with an amount of α-cyclodextrin or a functional derivative thereof sufficient to solubilise the cyclosporin in water.

In a further aspect of the present invention, there is provided a method of suppressing the mammalian immune system by administering to a mammal an effective amount of at least one cyclosporin in association with sufficient α-cyclodextrin or a functional derivative thereof to solubilise said cyclosporin.

DETAILED DESCRIPTION OF THE INVENTION

As currently commercially available, cyclosporin is supplied as a mixture in which the principal ingredient is cyclosporin A and which also contains significant, but much smaller, quantities of the other cyclosporins, specifically cyclosporins B, C, D and G. However, as already explained, the present invention can be applied either to a pure cyclosporin (whether cyclosporin A or another member of the cyclosporin group) or to a mixture of individual cyclosporins, such as the above-mentioned commercial mixture, e.g., cyclosporin A or a mixture of cyclosporin A with at least one other cyclosporin.

The discovery on which the present invention is based has several surprising features which could not have been anticipated on the basis of conventional thinking. Thus, although it is already known that the cyclodextrin will form inclusion compounds with other compounds and will thereby increase the solubility of these latter compounds, this formation of inclusion compounds has been limited to situations in which the hydrophobic cavity (which is several Angstrom units, i.e., several tenths of a nanometer, in diameter) can accommodate the guest compound. No example has been found of a cyclodextrin forming a clathrate in a case, such as the present, where the guest compound is not particularly hydrophobic in its solubility characteristics, has a molecular weight as large as 1,200, and has a cyclic structure.

We have, moreover, found that whereas β-cyclodextrin or γ-cyclodextrin can increase the solubility of cyclosporin by perhaps about twice, α-cyclodextrin can increase the solubility of cyclosporin by several orders of magnitude. Since α-cyclodextrin has the smallest diameter cavity among these three cyclodextrins and the cyclosporins are relatively large compounds, this is most unexpected. Both of these factors indicate very strongly that the solubilising effect achieved by α-cyclodextrin is not based simply (or, perhaps, at all) on the formation of a conventional cyclodextrin inclusion compound.

Apart from α-cyclodextrin itself, we have found that the increase in solubility achieved with α-cyclodextrin is also achieved with a variety of derivatives of α-cyclodextrin, provided that the essential structure and size of the α-cyclodextrin molecule are retained. Also, of course, since the composition is intended for therapeutic use, the solubilising compounds used must be physiologically tolerable. Examples of α-cyclodextrin derivatives which may be used include:

pharmaceutically acceptable esters in which some or all of the hydroxy groups in the glucose units have been acylated; there is no particular limitation upon the nature of the acyl units, provided that the resulting compounds are pharmaceutically acceptable and any acyl groups, whether they be derived from carboxylic, sulfonic or other physiologically tolerable acids may be employed; preferred examples of such groups include: groups derived from carboxylic acids, such as acetic acid, propionic acid, butyric acid, valeric acid, isovaleric acid, pivalic acid, fumaric acid, succinic acid, citric acid, tartaric acid, oxalic acid or maleic acid; groups derived from organic sulfonic acids, such as the lower alkylsulfonic acids (e.g., methanesulfonic acid, trifluoromethanesulphonic acid or ethanesulfonic acid) and arylsulfonic acids (e.g., benzenesulfonic acid or p-toluenesulfonic acid); and groups derived from amino acids, such as glutamic acid or aspargic acid; methylated α-cyclodextrin;

ether derivatives of α-cyclodextrin, particularly those in which the ether moiety is an alkyl group having from 1 to 4 carbon atoms;

aminoalkylated derivatives of α-cyclodextrin, particularly those in which the alkyl group has from 1 to 4 carbon atoms, for example, aminomethyl-α-cyclodextrin or aminoethyl-α-cyclodextrin;

sulfur-containing derivatives, particularly those formed with sulfur-containing acids such as α-cyclodextrin sulfate;

carboxyalkylated derivatives of α-cyclodextrin, particularly those in which the alkyl group has from 1 to 4 carbon atoms, such as carboxymethyl-α-cyclodextrin, carboxyethyl-α-cyclodextrin or carboxypropyl-α-cyclodextrin;

derivatives in which a monosaccharide or disaccharide has been condensed with one of the hydroxy groups of the α-cyclodextrin molecule, for example, those derived from maltose, glucose, fructose, galactose, sucrose or lactose; and polymers containing α-cyclodextrin in the main chain or pendant from the main chain, for example, those disclosed in "Cyclodextrins and their inclusion complexes" by J. Szejtli (Akademiai Kiado, Budapest, 1982).

There is no particular limit on the quantity of α-cyclodextrin which may be employed in order to achieve a solubilising effect and any amount of α-cyclodextrin will achieve some degree of solubilisation. In general, all other factors being equal, it would seem that, the higher the proportion of α-cyclodextrin, the greater the solubilising effect. We normally prefer a proportion of cyclosporin to α-cyclodextrin or derivatives thereof of from 1:0.5 to 1:1000, a ratio of from 1:1 to 1:200 by weight being more preferred.

The intended final use of the composition of the invention will dictate its physical form. For example, for oral preparations, the composition may be administered as an aqueous solution or as a solid preparation, such as powders, granules, capsules or tablets. For injection or as eye drops, the composition is employed as a solution, which may be supplied to the end user as a powder for making up with, e.g., water for injections or another suitable aqueous medium, or it may be supplied to the end user as a solution. All such formulations may be prepared by methods which are per se well known in the pharmaceutical art.

For example, at its simplest, the composition of the invention may comprise the cyclosporin and the α-cyclodextrin or derivative thereof as a mixture of powders. This mixture may be administered as such (normally orally), or may be kept as a powdery mixture until the point of use, at which time it is made up with water or another aqueous medium. Alternatively, the composition of the invention may be provided as a solution in water. In order to allow cyclosporin to be employed at a higher concentration than would otherwise be possible, it may be desirable to use an α-cyclodextrin derivative having a water-solubility greater than that of α-cyclodextrin itself. Alternatively, a water-miscible solvent capable of dissolving the cyclosporin may be added, for example, a simple alcohol such as ethanol, or a glycol such as propylene glycol or polyethylene glycol.

In addition, if required, there may be added the various additives commonly used in this field, such as pH adjustors, osmotic pressure regulators, antiseptics, surface active agents, flavours and masking agents, or any two or more thereof.

Where the composition of the invention is provided as a powdery mixture, this may be prepared by mixing the cyclosporin with the α-cyclodextrin and/or derivative thereof (and also any additives used) in powder form. Another method of providing a solid composition is by mixing the said ingredients in powder form, moistening the mixture with water or an aqueous solution of a water-miscible solvent, and then allowing the resulting pasty mixture to dry at ambient or under forced air circulation. Alternatively, a solution of the said ingredients in water or in an aqueous solution of a water-miscible solvent may be subjected to spray-drying or freeze-drying, which permits of easy sterilization and also gives a more uniform composition.

The composition of the invention may also be provided in the form of a solution, which may be either a solution prepared as above or a solution prepared by dissolving the spray-dried or freeze-dried powder in water or an aqueous solution of a water-miscible solvent. Where the composition of the invention is provided as a solution, we prefer that the concentration of α-cyclodextrin should be from 10 to 130 mg/ml, more preferably from 20 to 130 mg/ml, and that the concentration of cyclosporin should be from 0.1 to 2.0 mg/ml, more preferably from 0.2 to 1.5 mg/ml.

Although the cyclosporin and the α-cyclodextrin should be administered at essentially the same time in order to achieve the benefits of the present invention, it is not necessary that they be administered in admixture, especially where they are to be administered orally. In such a case, it is possible to administer the two components separately, provided that they are administered essentially simultaneously.

The invention is further described with reference to the following Examples, Comparative Examples and Experiments. The cyclosporin used in all of these was supplied by Sandoz Ltd. and pharmaceutical preparations thereof are commercially available from Sandoz Ltd. under the trade name "SANDIMMUNE".

EXAMPLE 1

0, 150, 300 or 500 mg of α-cyclodextrin were added to 4 separate portions each of 10 mg of cyclosporin, and 2,000 mg of α-cyclodextrin were added to a 50 mg portion of cyclosporin. 10 ml of water was then added to each of the resulting mixtures, and each mixture was stirred for about 15 hours at 25° C. At the end of this time, each mixture was filtered through a millipore filter and the quantity of cyclosporin in each filtrate was determined by HPLC (high pressure liquid chromatography). The solubilities were found to be 25, 70, 145, 300 and 1,900 μg/ml, respectively.

EXAMPLE 2

100 mg of cyclosporin and 10 g of α-cyclodextrin were dissolved in 50 ml of water. The solution was stirred for 2 hours at ambient temperature and then filtered through a millipore filter. The filtrate was frozen using a freezing mixture of dry ice and ethanol, which caused it to freeze-dry under reduced pressure. The powder obtained was then added to a volume of water equivalent to the volume of the filtrate obtained as described above, where it dissolved immediately to give a transparent aqueous solution.

COMPARATIVE EXAMPLE 1

0, 100, 200, 300, 500 or 1,000 mg of β-cyclodextrin were added to separate 10 mg portions of cyclosporin. 10 ml of water was then added to each of the resulting mixtures, and each mixture was stirred for about 15 hours at 25° C. and then filtered through a millipore filter. The amount of cyclosporin in each filtrate was determined by HPLC. The solubilities were found to be 25, 32, 43, 46, 45 and 44 μg/ml, respectively.

COMPARATIVE EXAMPLE 2

0, 1,000, 2,000, 3,000, 5,000 or 10,000 mg of γ-cyclodextrin were added to separate 10 mg portions of cyclosporin. 10 ml of water was then added to each of the resulting mixtures, and each mixture was stirred for about 15 hours at 25° C. and then filtered through a millipore filter. The amount of cyclosporin in each filtrate was determined by HPLC. The solubilities were found to be 28, 42, 62, 89, 80 and 75 μg/ml, respectively.

EXPERIMENT 1

Sample A 0.75 mg/ml of cyclosporin, 80 mg/ml of α-cyclodextrin and 6.57 mg/ml of sodium chloride were dissolved in distilled water for injections. To the solution was added a trace of a 0.01N aqueous solution of sodium hydroxide sufficient to raise its pH to about 7, after which the solution was filtered through a 0.22 μm filter. The cyclosporin concentration, relative osmotic pressure (against a physiological saline solution) and pH of the resulting solution (which was named "Sample A") were 0.75 mg/ml, 1.05 and 6.85, respectively.

Sample B

Peanut oil was heated to 40°–50° C., and 10 mg/ml of cyclosporin was dissolved in the hot oil. The solution was then cooled to ambient temperature.

Ocular Test 0.05 ml of either Sample A or Sample B was dropped into the right eye of a male Japanese white rabbit. This operation was carried out a total of 10 times at intervals of 30 minutes. 30 minutes after the last application, the cornea was excised. In order to ensure that the sample obtained was free from cyclosporin absorbed onto its surface, the corneal epithelium was removed at the same time.

This experiment was performed on three separate rabbits with each of Samples A and B, and the results were averaged. The average of the results from Samples A were 10,400 ng/ml, whilst the average of the results from Samples B was 5,400 ng/ml. The cyclosporin in the corneal parenchyma samples was analysed quantitatively using a radio-immunoassay kit produced by Sandoz Ltd. Although the cyclosporin concentration in solution in Sample A was less than one tenth of that in Sample B (0.75 mg/ml, against 10 mg/ml), the results shown above indicate that Sample A exhibited better tissue transfer, showing a bioavailability more than 20 times that of Sample B.

EXPERIMENT 2

Samples C, D and E 0.25 mg/ml of cyclosporin, 40 mg/ml of α-cyclodextrin and 7.79 mg/ml of sodium chloride (Sample C), or 0.10 mg/ml of cyclosporin, 20 mg/ml of α-cyclodextrin and 8.40 mg/ml of sodium chloride (Sample D) or 0.05 mg/ml of cyclosporin, 10 mg/ml of α-cyclodextrin, and 8.70 mg/ml of sodium chloride (Sample E) were dissolved in distilled water for injections. A trace of a 0.01N aqueous solution of sodium hydroxide was then added to each of these solutions to raise its pH to a value in the approximate region of 7, after which the solutions were filtered through a 0.22 μm filter. The cyclosporin concentrations, relative osmotic pressures (against physiological saline) and pH of the solutions were respectively as follows:

Sample C: 0.25 mg/ml, 1.04, 6.30;
Sample D: 0.09 mg/ml, 1.02, 6.86;
Sample E: 0.03 mg/ml, 1.02, 6.58.

Ocular Effects 0.05 ml of each of Samples A, C, D or E was applied in a single administration to the right eye of a male Japanese white rabbit. This administration was repeated a further 3 times (making 4 administrations in total) at intervals of 2 hours. 30 minutes after the last application, the cornea was excised as described in Experiment 1 and the cyclosporin levels in the corneal parenchyma were determined, also as in Experiment 1, averaging the results from 3 corneal samples. The results achieved were as follows:

A: 4900 ng/ml;
C: 4100 ng/ml;
D: 2200 ng/ml;
E: 1300 ng/ml.

The cyclosporin levels in the uvea were also determined and were found to be as follows:

A: 970 ng/ml;
C: 780 ng/ml;
D: 830 ng/ml;
E: 760 ng/ml.

This demonstrates that cyclosporin was successfully transferred into the ocular tissues. The level in the corneal parenchyma is important in relation to its use in keratoplasty, whilst that in the uvea is important in the treatment of Behcet's Syndrome.

We claim:

1. A pharmaceutical composition comprising a pharmaceutically acceptable carrier and a pharmaceutically effective amount of at least one cyclosporin in admixture with an amount of a functional derivative of α-cyclodextrin sufficient to solubilise the cyclosporin in water, wherein the α-cyclodextrin derivative is selected from the group consisting of α-cyclodextrin esters, α-cyclodextrin ethers, aminoalkylated derivatives of α-cyclodextrin, salts of α-cyclodextrin with a sulfur-containing acid, carboxyalkylated derivatives of α-cyclodextrin, addition compounds of α-cyclodextrin with a monosaccharide, addition compounds of α-cyclodextrin with a disaccharide, polymers comprising α-cyclodextrin in their main chain and polymers comprising α-cyclodextrin pendant on their main chain.

2. The composition of claim 1, wherein the weight ratio of said cyclosporin to said α-cyclodextrin derivative is from 1:0.5 to 1:1000.

3. The composition of claim 1, wherein the weight ratio of said cyclosporin to said α-cyclodextrin derivative is from 1:1 to 1:200.

4. The composition of claim 1, wherein the α-cyclodextrin derivative is selected from the group consisting of acetylated α-cyclodextrin, methylated α-cyclodextrin, aminoethyl-α-cyclodextrin, α-cyclodextrin sulfate and maltosylated α-cyclodextrin.

5. The composition of claim 1, wherein said cyclosporin is selected from the group consisting of cyclosporin A, cyclosporin B, cyclosporin D and cyclosporin G.

6. The composition of claim 1, wherein said α-cyclodextrin derivative is a α-cyclodextrin ester in which some or all of the hydroxy groups in the glucose units are acylated and the acyl groups are derived from an acid selected from the group consisting of (a) a carboxylic acid, said carboxylic acid selected from the group consisting of acetic acid, propionic acid, butyric acid, valeric acid, isovaleric acid, pivalic acid, fumaric acid, succinic acid, citric acid, tartaric acid, oxalic acid and maleic acid; (b) a sulfonic acid, said sulfonic acid selected from the group consisting of methanesulfonic acid, trifluoromethane sulfonic acid, ethanesulfonic acid, benzenesulfonic acid and p-toluene sulfonic acid; and (c) an amino acid, said amino acid selected from the group consisting of glutamic acid and aspargic acid.

7. The composition of claim 1, wherein said α-cyclodextrin derivative is an ether derivative wherein the ether moiety is an alkyl group having 1 to 4 carbon atoms.

8. The composition of claim 1, wherein said α-cyclodextrin derivative is an aminoalkylated derivative of α-cyclodextrin wherein the alkyl group has 1 to 4 carbon atoms.

9. The composition of claim 8, wherein the aminoalkylated derivative of α-cyclodextrin is selected from the group consisting of aminomethyl-α-cyclodextrin and aminoethyl-α-cyclodextrin.

10. The composition of claim 1, wherein said α-cyclodextrin derivative is a carboxyalkylated derivative having an alkyl group with 1 to 4 carbon atoms.

11. The composition of claim 10, wherein said carboxyalkylated derivative is selected from the group consisting of carboxymethyl-α-cyclodextrin, carboxyethyl-α-cyclodextrin and carboxypropyl-α-cyclodextrin.

12. The composition of claim 1, wherein said α-cyclodextrin derivative is an addition compound of α-cyclodextrin comprising a monosaccharide or a disaccharide which is condensed with a hydroxy group of an α-cyclodextrin derived from maltose, glucose, fructose, galactose, sucrose or lactose.

13. A pharmaceutical composition comprising a pharmaceutically acceptable carrier and a pharmaceutically effective amount of at least one cyclosporin in admixture with an amount of α-cyclodextrin sufficient to solubilise the cyclosporin in water.

14. The composition of claim 13, wherein the weight ratio of said cyclosporin to said α-cyclodextrin is from 1:0.5 to 1:1000.

15. The composition of claim 13, wherein the weight ratio of said cyclosporin to said α-cyclodextrin is from 1:1 to 1:200.

16. A pharmaceutical composition comprising a pharmaceutically acceptable carrier and a pharmaceutically effective amount of at least one cyclosporin and α-cyclodextrin or a functional derivative thereof dissolved in water, the amount of α-cyclodextrin or said functional derivative thereof being sufficient to solubilise the cyclosporin in the water, wherein the α-cyclodextrin derivative is selected from the group consisting of α-cyclodextrin esters, α-cyclodextrin ethers, aminoalkylated derivatives of α-cyclodextrin, salts of α-cyclodextrin with a sulfur-containing acid, carboxyalkylated derivatives of α-cyclodextrin, addition compounds of α-cyclodextrin with a monosaccharide, addition compounds of α-cyclodextrin with a disaccharide, polymers comprising α-cyclodextrin in their main chain and polymers comprising α-cyclodextrin pendant on their main chain.

17. The composition of claim 16, wherein the weight ratio of said cyclosporin to said α-cyclodextrin or derivative thereof is from 1:0.5 to 1:1000.

18. The composition of claim 16, wherein the weight ratio of said cyclosporin to said α-cyclodextrin or derivative thereof is from 1:1 to 1:200.

19. A method of suppressing the mammalian immune system by administering to a mammal a pharmaceutically effective amount of at least one cyclosporin in association with sufficient α-cyclodextrin or a functional derivative thereof to solubilise said cyclosporin, wherein the α-cyclodextrin derivative is selected from the group consisting of α-cyclodextrin esters, α-cyclodextrin ethers, aminoalkylated derivatives of α-cyclodextrin, salts of α-cyclodextrin with a sulfur-containing acid, carboxyalkylated derivatives of α-cyclodextrin, addition compounds of α-cyclodextrin with a monosaccharide, addition compounds of α-cyclodextrin with a disaccharide, polymers comprising α-cyclodextrin in their main chain and polymers comprising α-cyclodextrin pendant on their main chain.

20. The method of claim 19, wherein said cyclosporin and said α-cyclodextrin or derivative thereof are administered in admixture.

21. The method of claim 19, wherein said cyclosporin and said α-cyclodextrin or derivative thereof are administered separately, but essentially simultaneously.

22. The method of claim 19, wherein the α-cyclodextrin derivative is selected from the group consisting of acetylated α-cyclodextrin, methylated α-cyclodextrin, aminoethyl-α-cyclodextrin, α-cyclodextrin sulfate and maltosylated α-cyclodextrin.

23. The method of claim 19, wherein the weight ratio of said cyclosporin to said α-cyclodextrin or derivative thereof is from 1:0.5 to 1:1000.

24. The method of claim 19, wherein the weight ratio of said cyclosporin to said α-cyclodextrin or derivative thereof is from 1:1 to 1:200.

25. The method of claim 19, wherein the administering is orally, by injection, or as eyedrops.

26. A method of suppressing the mammalian immune system by administering to a mammal a pharmaceutically effective amount of at least one cyclosporin in association with α-cyclodextrin, the weight ratio of said cyclosporin to said α-cyclodextrin being from 1:0.5 to 1:1000.

27. The method of claim 26, wherein the weight ratio of said cyclosporin to said α-cyclodextrin is from 1:1 to 1:200.

28. A pharmaceutical composition comprising (a) a pharmaceutically acceptable carrier, (b) a pharmaceutically effective amount of cyclosporin A or a mixture of cyclosporin A with at least one other cyclosporin in admixture with (c) an amount of a functional derivative of α-cyclodextrin sufficient to solubilise said cyclosporin in water, wherein the α-cyclodextrin derivative is selected from the group consisting of α-cyclodextrin esters, α-cyclodextrin ethers, aminoalkylated derivatives of α-cyclodextrin, salts of α-cyclodextrin with a sulfur-containing acid, carboxyalkylated derivatives of α-cyclodextrin, addition compounds of α-cyclodextrin with a monosaccharide, addition compounds of α-cyclodextrin with a disaccharide, polymers comprising α-cyclodextrin in their main chain and polymers comprising α-cyclodextrin pendant on their main chain.

29. A pharmaceutical composition comprising (a) a pharmaceutically acceptable carrier, (b) a pharmaceutically effective amount of cyclosporin A or a mixture of cyclosporin A with at least one other cyclosporin in admixture with (c) an amount of α-cyclodextrin sufficient to solubilise said cyclosporin in water.

30. A method of suppressing the mammalian immune system by administering to a mammal a pharmaceutically effective amount of (a) cyclosporin A or a mixture of cyclosporin A with at least one other cyclosporin in association with (b) a sufficient amount of a functional derivative of α-cyclodextrin to solubilise said cyclosporin, wherein the α-cyclodextrin derivative is selected from the group consisting of α-cyclodextrin esters, α-cyclodextrin ethers, aminoalkylated derivatives of α-cyclodextrin, salts of α-cyclodextrin with a sulfur-containing acid, carboxyalkylated derivatives of α-cyclodextrin, addition compounds of α-cyclodextrin with a monosaccharide, addition compounds of α-cyclodextrin with a disaccharide, polymers comprising α-cyclodextrin in their main chain and polymers comprising α-cyclodextrin pendant on their main chain.

31. The method of claim 30, wherein the administering is orally, by injection, or as eyedrops.

32. A method of suppressing the mammalian immune system by administering to a mammal a pharmaceutically effective amount of (a) cyclosporin A or a mixture of cyclosporin A with at least one other cyclosporin in association with (b) sufficient α-cyclodextrin to solubilise said cyclosporin.

33. The method of claim 32, wherein the administering is orally, by injection, or as eyedrops.

* * * * *